(12) United States Patent
Trajano et al.

(10) Patent No.: US 11,844,855 B2
(45) Date of Patent: Dec. 19, 2023

(54) SUN CARE COMPOSITION FOR WHITENING THE SKIN, USE OF THE SUN CARE COMPOSITION, AND PROCESS OF MANUFACTURE OF THE SUN CARE COMPOSITION

(71) Applicant: L'Oreal, Paris (FR)

(72) Inventors: Patricia Trajano, Rio de Janeiro (BR); Angeles Fonolla-Moreno, Rio de Janeiro (BR); Renata Souto Maior Afonso Ferreira, Rio de Janeiro (BR)

(73) Assignee: L'Oreal, Paris (FR)

( * ) Notice: Subject to any disclaimer, the term of this patent is extended or adjusted under 35 U.S.C. 154(b) by 133 days.

(21) Appl. No.: 17/264,880

(22) PCT Filed: Jul. 31, 2018

(86) PCT No.: PCT/BR2018/050265
§ 371 (c)(1),
(2) Date: Feb. 1, 2021

(87) PCT Pub. No.: WO2020/024022
PCT Pub. Date: Feb. 6, 2020

(65) Prior Publication Data
US 2021/0251871 A1    Aug. 19, 2021

(51) Int. Cl.
| | | |
|---|---|---|
| *A61K 8/60* | (2006.01) | |
| *A61K 8/9794* | (2017.01) | |
| *A61K 8/9789* | (2017.01) | |
| *A61K 8/35* | (2006.01) | |
| *A61K 8/368* | (2006.01) | |
| *A61K 8/49* | (2006.01) | |
| *A61Q 17/04* | (2006.01) | |
| *A61Q 19/02* | (2006.01) | |

(52) U.S. Cl.
CPC ............ *A61K 8/602* (2013.01); *A61K 8/35* (2013.01); *A61K 8/368* (2013.01); *A61K 8/498* (2013.01); *A61K 8/4966* (2013.01); *A61K 8/9789* (2017.08); *A61K 8/9794* (2017.08); *A61Q 17/04* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 2004/0166069 A1 | | 8/2004 | Gupta |
| 2017/0112736 A1* | | 4/2017 | Meyer ................ A61Q 5/02 |

FOREIGN PATENT DOCUMENTS

| | | | | |
|---|---|---|---|---|
| CN | 106 389 216 A | | 2/2017 | |
| CN | 106852768 A | * | 6/2017 | ............ A61K 8/347 |
| CN | 108309821 A | * | 7/2018 | ............ A61K 8/02 |
| FR | 2 760 191 A1 | | 9/1998 | |

OTHER PUBLICATIONS

Anonymous "Radiance Boosting Antioxidant Serum" GNPD Online Database, Jun. 12, 2017.
Su-Tze Chou et al. "Cinnamomum Cassia Essential Oil Inhibits [alpha]-MSH-Induced Melanin Production and Oxidative Stress in Murine B16 Melanoma Cells" Int. J. Mol. Sci., vol. 14 No. 9, Sep. 18, 2013, pp. 19186-19201.
Asano Y et al "Topical composition for cosmetics, comprises skin whitening agent, plant extract(s), anti-inflammatory agent(s) and antioxidant" WIP/Thomson, vol. 2000, No. 35, Apr. 25, 2000.
PCT International Search Report for PCT/BR2018/050265 dated Apr. 23, 2019.

* cited by examiner

*Primary Examiner* — Nannette Holloman
(74) *Attorney, Agent, or Firm* — McNees Wallace & Nurick LLC

(57) ABSTRACT

The present invention relates to a cosmetic composition to be used on the skin comprising the combination of a particular whitening system, a UVA filter system, and a combination of antioxidants for effectively whitening the skin, in particular the skin of the face, while also protecting these materials from the damages caused by UVA radiation.

34 Claims, 2 Drawing Sheets

SUN CARE COMPOSITION FOR WHITENING THE SKIN, USE OF THE SUN CARE COMPOSITION, AND PROCESS OF MANUFACTURE OF THE SUN CARE COMPOSITION

FIELD OF THE INVENTION

The present invention relates to a sun care composition to be used on the skin comprising a particular combination of a whitening system, a UVA filter system, and a combination of antioxidants for effectively whitening the skin, in particular the skin of the face while also protecting it from the damages caused by UVA radiation.

BACKGROUND OF THE INVENTION

The color of human skin is mainly determined by the nature and concentration of a pigment, melanin.

At different periods of their life, especially during aging and as a result of UVA radiation, some people see appear on their skin, particularly on their hands and/or face, darker and/or more pigmented spots, giving the skin a heterogeneity appearance. These spots are due in particular to a high concentration of melanin in the keratinocytes located on the surface of the skin.

The mechanism of melanogenesis, that is, the mechanism of melanin formation is particularly complex, and schematically involves the following main steps:

Tyrosine is involved in the mechanism of skin pigmentation, which schematically involves the following main steps:

Tyrosine→DOPA→Dopaquinone→Dopachrome→Melanin

Tyrosinase is the essential enzyme involved in these reactions. In particular, it catalyzes the conversion reaction of tyrosine to DOPA (dihydroxyphenylalanine) thanks to its hydroxylase activity, and the conversion reaction of DOPA to dopaquinone by virtue of its oxidase activity. This tyrosinase only acts when it is maturing under the influence of certain biological factors.

In addition, UVA radiation can have a significant contribution to the clinical consequences of solar UV exposure, particularly the pigmentation caused by the solar radiation.

UVA induces immediate pigment darkening (IPD) within a short time, as little as a few hours, by acting on preexisting melanin. UVA can also cause persistent pigment darkening (PPD) in the skin. Among the UV wavelengths reaching the Earth surface, longwave UVA (340-400 nm) represents up to 80% of total UV and show high penetration properties, reaching the deep dermis.

When a person already has spots on the skin, or melasma (skin discoloration), a possible solution to decrease their color is to use some active ingredients that act in the hyperpigmentation process. Although UVA reaches the dermal layers of the skin and its effects on photo aging and keratinocyte invasiveness, melanocytes seem to be more susceptible to the damaging effects of UVA. For example, exposure of cultured melanocytes and keratinocytes from the same donor to UVA and UVB showed that UVA-induced oxidative lesions contributed to a larger extent to DNA damage in melanocytes than in keratinocytes.

Since human skin is daily exposed to solar UVA radiation, the use of harmless topical depigmenting substances having a good efficacy is particularly sought for whitening pigmented spots. However, the products available on the market either whitens the skin, or protects it from sun damaging (that is, from generating new dark areas). None of these products is capable of progressively whitening the skin, while also preventing the formation of new dark areas.

In addition, it is desired a composition that not only whitens the melasmas provoked by the sun, while preventing their formation, but also that progressively depigment these melasmas.

Thus, the inventors succeeded to overcome the problems of the state of the art and surprisingly revealed a sun care composition for whitening the skin, while also protecting it from further darkening caused by UVA rays. Said composition comprises a particular combination of a whitening system and a UVA filter system.

SUMMARY OF THE INVENTION

The present invention is directed to provide a sun care composition for whitening the skin, said composition comprising a whitening system and a UVA filter system for progressive whitening and preventing dark-spots on human skin.

Particularly, it is an objective of the present invention to provide, as a single formulation, a product with the association of two different mechanisms against the action of the sun in the development of skin melasmas. The first action comes from the activity of the UVA filters of the UVA filter system and the second action comes from the activity of the whitening actives of the whitening system.

In other words, the sun care composition of the present invention not only whitens pre-existing melasmas/dark spots, having a progressively depigmentation effect due to its prolonged use, but also prevents the formation of new melasmas/dark spots on the skin.

The inventors of the present invention have surprisingly found that the sun care composition for whitening and preventing the formation of dark areas also have a progressive whitening effect.

BRIEF DESCRIPTION OF THE DRAWINGS

The accompanying drawings, which are included to provide a further understanding of the invention and are incorporated in and constitute a part of this specification, together with the description, serve to explain the principles of the invention.

The FIG. 1 is a graphic representing the evolution in time of the hyperpigmentation degree of the subjects of Example 11.

Figure 1:
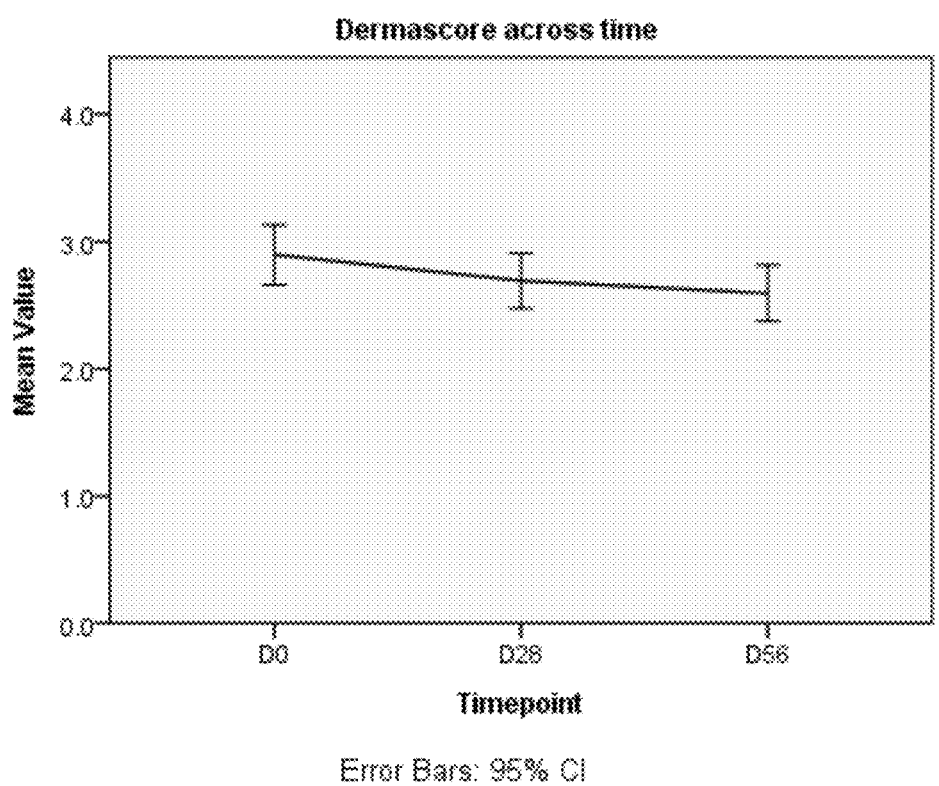
Figure 2:
Figure 2:
Figure 2:
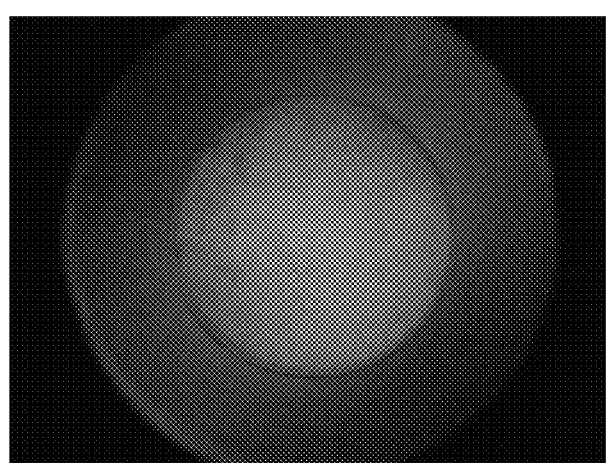

The FIG. 2 (a) to (c) are pictures demonstrating the improvement of the hyperpigmentation degree of the skin from a subject of Example 11.

DETAILED DESCRIPTION OF THE INVENTION

The sun care composition for whitening the skin of the present invention comprises:
  (a) a UVA filter system;
  (b) a whitening system comprising neohesperidin dihydrochalcone, capryloyl salicylic acid and dipotassium glycyrrhizate; and
  (c) a combination of at least two antioxidants selected from at least one vitamin and at least one vegetal extract, wherein the at least one vitamin is selected from tocopherol, and the at least one vegetal extract is selected from *Zingiber officinale* (ginger) root extract, Sanguisorba officinalis root extract, Cinnamomum cassia bark extract or their mixtures.

The composition according to the invention provides depigmentation results regarding dark spots and/or melasmas on the skin, while protecting these materials from further damages provoked by the sun, particularly the UVA radiation.

UVA Filter System

In a preferred embodiment, the suitable UVA filter system comprises at least three UVA filters selected from butyl methoxydibenzoylmethane, bis-ethylhexyloxyphenol methoxyphenyl triazine and ethylhexyl triazone.

The UVA system may be presented in the composition of the present invention in a range of from about 1% to about 15% by weight, preferably from about 5% to about 10% by weight, based on the total weight of the composition.

Also, the UVA filter system employs a first UVA filter in an amount ranging from about 1% to about 7% by weight and preferably from about 2.5% to about 4% by weight, including all ranges and sub-ranges there between, relative to the total weight of the composition.

The UVA filter system employs a second UVA filter in an amount preferably ranging from about 1% to about 7% by weight and preferably from about 2.5% to about 4% by weight, including all ranges and sub-ranges there between, relative to the total weight of the composition.

The UVA filter system employs a third UVA filter in an amount preferably ranging from about 1% to about 7% by weight and preferably from about 2% to about 5% by weight, including all ranges and sub-ranges there between, relative to the total weight of the composition.

Whitening System

A substance is recognized as depigmenting if it acts directly on the vitality of the epidermal melanocytes where the melanogenesis takes place, and/or if it interferes with one of the stages of melanin biosynthesis either by inhibiting one of the enzymes involved in melanogenesis, or by interposing itself as a structural analogue of one of the chemical compounds of the melanin synthesis chain, which can then be blocked and thus ensure depigmentation.

The suitable whitening system of the present invention comprises at least three different whitening actives, which act at different levels of the pigmentation of the melasma in order to whiten it.

Preferably, the whitening system of the present invention comprises neohesperidin dihydrochalcone, capryloyl salicylic acid and dipotassium glycyrrhizate.

Neohesperidin dihydrochalcone is a powerful antioxidant which inhibits the production of melanosomes, acting as a tyrosinase indirect inhibitor, while capryloyl salicylic acid acts as a cellular renovator, removing hyperpigmented cells of stratum corneum, and dipotassium glycyrrhizate shortens the dendrites, preventing the melanin from reaching the skin surface.

In a preferred embodiment, the amount of the whitening system is ranging from about 0.05% to about 5% by weight, preferably from about 0.1% to about 2.5% by weight, including all ranges and sub-ranges there between, relative to the total weight of the composition.

The whitening system employs neohesperidin dihydrochalcone in an amount preferably ranging from about 0.05% to about 3% by weight and preferably from about 0.1% to about 1.5% by weight, including all ranges and sub-ranges there between, relative to the total weight of the composition.

The whitening system employs capryloyl salicylic acid in an amount preferably ranging from about 0.05% to about 2.5% by weight and preferably from about 0.05% to about 1.5% by weight, including all ranges and sub-ranges there between, relative to the total weight of the composition.

The whitening system employs dipotassium glycyrrhizate in an amount preferably ranging from about 0.05% to about 3% by weight and preferably from about 0.1% to about 2% by weight, including all ranges and sub-ranges there between, relative to the total weight of the composition.

Antioxidizing Agents

The combination of at least two antioxidants suitable for the present invention is selected from at least one vitamin and at least one vegetal extract.

Preferably, the vitamin is selected from tocopherol and the vegetal extract is selected from Zingiber officinale (ginger) root extract, Sanguisorba officinalis root extract, Cinnamomum cassia bark extract or their mixtures.

In a preferred embodiment, the combination of at least one antioxidant vitamin and at least one antioxidant vegetal extract is selected from tocopherol and a vegetal extract comprising Zingiber officinale (ginger) root extract, Sanguisorba officinalis root extract, and Cinnamomum cassia bark extract.

In a preferred embodiment, the amount of a combination of at least two antioxidants is ranging from about 0.05% to 5% by weight and preferably from about 0.1% to about 2.5% by weight, including all ranges and sub-ranges there between, relative to the total weight of the composition.

The combination of at least two antioxidants employs a vitamin in an amount preferably ranging from about 0.05% to about 2.5% by weight and preferably from about 0.75% to about 1.5% by weight, including all ranges and sub-ranges there between, relative to the total weight of the composition.

The combination of at least two antioxidants employs a vegetal extract in an amount preferably ranging from about 0.05% to about 3.75% by weight and preferably from about 0.1% to about 2% by weight, including all ranges and sub-ranges therebetween, relative to the total weight of the composition.

In addition, the pH of the sun care composition of the invention is preferably within the range of about 5.5 to about 7 more preferably, of about 6.5

Furthermore, the sun care composition of the present invention may present a Sun Protection Factor ranging from 30 to 80, preferably of about 60.

The sun care composition of the invention can be used as a daily product for the skin.

In a preferred embodiment, the composition of the invention is for the manufacture of a product for progressive whitening the skin, while preventing further damages form the UVA radiation.

Another preferred embodiment is direct to a process for the manufacturing the sun care composition for whitening the skin.

A further preferred embodiment is related to the use of a sun care composition for the manufacture of a product to be used for whitening the skin, preferably for the manufacture of a product for progressive whitening skin, while preventing further damages form the UVA radiation.

In addition, the sunscreen composition according to the present invention is cutaneous safe.

Terms

As used herein, the expression "at least" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

Additional UV Filters

The composition of the present invention may further comprise additional non-limiting UV filters.

Suitable UV filter system of the present invention comprises, for example, terephthalylidene dicamphor sulfonic acid, octocrylene and butyl methoxydibenzoylmethane sulfonic acid.

According to the invention, the concentration of additional sunscreen/UV filters in the system may be between about 5% to about 35%, preferably between about 7% to about 30% and even more preferably between about 10 to about 29% by weight of the total weight of the composition.

Other additional suitable additional UV filters may be selected as follows:

Oil-Soluble Organic Sunscreen Ingredient

The "oil-soluble organic sunscreen ingredient" means any organic compound for screening out UV radiation, which can be fully dissolved in molecular form or miscible in an oil phase or which can be dissolved in colloidal form (for example in micellar form) in an oil fatty phase.

Non-limiting examples of oil-soluble organic sunscreen ingredients useful in the invention include, for example, cinnamic derivatives; anthranilates; salicylic derivatives; dibenzoylmethane derivatives; camphor derivatives; benzophenone derivatives; diphenylacrylate derivatives; triazine derivatives; benzotriazole derivatives; benzalmalonate derivatives, especially those cited in U.S. Pat. No. 5,624,663, benzimidazole derivatives; imidazolines; bis-benzoazolyl derivatives as described in patents EP669323 and U.S. Pat. No. 2,463,264, p-aminobenzoic acid (PABA) derivatives; methylene bis(hydroxyphenylbenzotriazole) derivatives as described in applications U.S. Pat. Nos. 5,237,071, 5,166,355, GB2303549, DE19726184 and EP893119; benzoxazole derivatives as described in patent applications EP0832642, EP1027883, EP1300137 and DE10162844; screening polymers and screening silicones such as those described especially in patent application WO 93/04665; dimers derived from alkyl-styrene such as those described in patent application DE 19855649; 4,4-diarylbutadienes such as those described in patent applications EP0967200, DE19746654, DE19755649, EP-A-1008586, EP1133980 and EP1133981, merocyanine derivatives such as those described in patent applications WO 04/006878, WO 05/058269 and WO 06/032741; and mixtures thereof, the entire contents of the patents and patent applications being incorporated by reference in their entirety.

As examples of other suitable oil-soluble organic sunscreen ingredients, mention may be made of those denoted hereinbelow under their INCI name:

Cinnamic Derivatives:

Examples of suitable cinnamic derivatives include, but are not limited to, ethylhexyl methoxycinnamate, isopropyl methoxycinnamate, isoamyl methoxycinnamate, DEA methoxycinnamate, diisopropyl methylcinnamate, glyceryl ethylhexanoate dimethoxycinnamate.

Dibenzoylmethane Derivatives:

Examples of suitable dibenzoylmethane derivatives include, but are not limited to, butyl methoxydibenzoylmethane and isopropyl dibenzoylmethane.

Salicylic Derivatives:

Examples of suitable salicylic derivatives include, but are not limited to, homosalate, ethylhexyl salicylate, dipropylene glycol salicylate and TEA salicylate.

Beta, Beta-Diphenylacrylate Derivatives:

Examples of suitable beta, beta-diphenylacrylate derivatives include, but are not limited to, octocrylene and etocrylene.

Benzophenone Derivatives:

Examples of suitable benzophenone derivatives include, but are not limited to, benzophenone-1, benzophenone-2, benzophenone-3 or oxybenzone, benzophenone-4, benzophenone-5, benzophenone-6, benzophenone-8, benzophenone-9, benzophenone-12, n-hexyl 2-(4-diethylamino-2-hydroxybenzoyl)benzoate+" or as a mixture with octyl methoxycinnamate.

Benzylidenecamphor Derivatives:

Examples of suitable benzylidenecamphor derivatives include, but are not limited to, 3-benzylidene camphor manufactured, 4-methylbenzylidene camphor, polyacrylamidomethyl benzylidene camphor manufactured.

Phenylbenzotriazole Derivatives:

Examples of suitable phenylbenzotriazole derivatives include, but are not limited to, drometrizole trisiloxane, methylene bis-benzotriazolyl tetramethylbutyl-phenol, or in micronized form as an aqueous dispersion.

Triazine Derivatives:

Examples of suitable triazine derivatives include, but are not limited to, bis-ethylhexyloxyphenol methoxyphenyl triazine, ethylhexyl triazone, diethylhexyl butamido triazone, 2,4,6-tris(dineopentyl 4'-aminobenzalmalonate)-s-triazine, 2,4,6-tris(diisobutyl 4'-aminobenzalmalonate)-s triazine, 2,4-bis(dineopentyl 4'-aminobenzalmalonate)-6-(n-butyl 4'-aminobenzoate)-s-triazine, symmetrical triazine screening agents described in U.S. Pat. No. 6,225,467, patent application WO 2004/085412 (see compounds 6 and 9) or the document "Symmetrical Triazine Derivatives" IP.COM Journal, IP.COM Inc., West Henrietta, N.Y., US (20 Sep. 2004), especially 2,4,6-tris(biphenyl)-1,3,5-triazines (in particular 2,4,6-tris(biphenyl-4-yl)-1,3,5-triazine and 2,4,6-tris(terphenyl)-1,3,5-triazine, which is included in patent applications WO 06/035000, WO 06/034982, WO 06/034991, WO 06/035007, WO 2006/034992 and WO 2006/034985).

Anthranilic Derivatives:

An example of a suitable anthranilic derivative includes, but is not limited to, methyl anthranilate.

Imidazoline Derivatives:

An example of a suitable imidazoline derivative includes, but is not limited to, ethylhexyl dimethoxybenzylidene dioxoimidazoline propionate.

Benzalmalonate Derivatives:

An example of a suitable benzalmalonate derivative includes, but is not limited to, polyorganosiloxane containing benzalmalonate functions, for instance polysilicone-15.

4,4-Diarylbutadiene Derivatives:

Examples of a suitable 4,4-diarylbutadiene derivative includes, but is not limited to, 1-Dicarboxy(2,2'-dimethylpropyl)-4,4-diphenyl-butadiene.

Benzoxazole Derivatives:

An example of suitable benzoxazole derivative includes, but is not limited to, 2,4-bis[5-(1-dimethylpropyl)benzoxazol-2-yl-(4-phenyl)imino]-6-(2-ethylhexyl)imino-1,3,5-triazine, and mixtures thereof.

Preferably, the oil-soluble organic sunscreen ingredient will be chosen from butyl methoxydibenzoylmethane, ethylhexyl salicylate, ethylhexyl triazone, octocrylene, drometrizole trisiloxane, bis-ethylhexyloxyphenol methoxyphenyl triazine, and mixtures thereof.

The oil-soluble organic sunscreen ingredient is preferably present in the composition according to the invention in an amount of from about 3% to about 25% by weight, preferably in an amount of from about 5% to about 20% by weight, and most preferably about 7% to about 18% by weight, based on the total weight of the composition.

Water-Soluble Organic Sunscreen Ingredient

The "water-soluble organic sunscreen ingredient" means any organic compound for screening out UV radiation, which can be fully dissolved in molecular form or miscible in a liquid aqueous phase or which can be dissolved in colloidal form (for example in micellar form) in a liquid aqueous phase.

Non-limiting examples of water-soluble organic sunscreen ingredients useful in the invention include, for example, terephthalylidene dicamphor sulfonic acid, phenylbenzimidazole sulfonic acid, benzophenone-4, aminobenzoic acid (PABA), 4-Bis(polyethoxy)-para-aminobenzoic acid polyethoxyethyl ester (PEG-25 PABA), camphor benzalkonium methosulfate, methylene bis-benzotriazolyl tetramethylbutylphenol (Bisoctrizole), disodium phenyl dibenzimidazole tetrasulfonate (Bisdisulizole disodium), and tris-biphenyl triazine; their derivatives and corresponding salts; naphthalene bisimide derivatives such as those described in European patent application EP1990372 A2, the entire contents of which is hereby incorporated by reference; and cinnamido amine cationic quaternary salts and derivatives such as those described in U.S. Pat. No. 5,601,811, the entire contents of which is hereby incorporated by reference, and mixtures thereof.

The salts of the compounds that may be used according to the invention are chosen in particular from salts of alkali metals, for example sodium or potassium; salts of alkaline-earth metals, for example calcium, magnesium or strontium; metal salts, for example zinc, aluminum, manganese or copper; salts of ammonium of formula $NH4+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts. Salts chosen from sodium, potassium, magnesium, strontium, copper, manganese or zinc salts are preferably used. The sodium salt is preferably used.

Preferably, the water-soluble organic sunscreen ingredient will be chosen from terephthalylidene dicamphor sulfonic acid, methylene bis-benzotriazolyl tetramethylbutylphenol, and mixtures thereof.

The water-soluble organic sunscreen ingredient is preferably present in the composition according to the invention in an amount of from about 0.1% to about 10% by weight, preferably in an amount of from about 0.5% to about 8% by weight, and most preferably about 1% to about 7% by weight, based on the total weight of the composition.

Silica-Coated Titanium Dioxide Sunscreen Ingredient

The "silica-coated titanium dioxide sunscreen ingredient" means spherical beads which are formed by encapsulating titanium dioxide particles in silica.

Non-limiting examples of silica coated titanium dioxide sunscreen ingredients useful in the invention include, for example, titanium dioxide coated with silica, such as name silica (and) titanium dioxide having a composition of silica: titanium dioxide of about 55:45 and having a particle size from about 2 microns to about 7 microns.

The silica-coated titanium dioxide sunscreen ingredient is preferably present in the composition according to the invention in an amount of from about 1% to about 10% by weight, preferably in an amount of from about 2% to about 10% by weight, and most preferably about 5% to about 10% by weight, based on the total weight of the composition.

Additional Ingredients

In addition to the essential components described hereinbefore, the composition of the invention may further comprise any usual cosmetically acceptable ingredient, which may be chosen especially from such as additional sunscreens, perfume/fragrance, preserving agents, solvents, actives, surfactants, fatty compounds, vitamins, fillers, silicones, polymers, pigments and mixtures thereof.

A person skilled in the art will take care to select the optional additional ingredients and/or the amount thereof such that the advantageous properties of the composition according to the invention are not, or are not substantially, adversely affected by the envisaged addition.

Suitable polymers include, but are not limited to, aluminum starch octenylsuccinate, xanthan gum, poly 010-30 alkyl acrylate, acrylates/$C_{10-30}$ alkyl acrylate crosspolymer, styrene/acrylates copolymer, and mixtures thereof.

The composition may also comprise at least one silicon ingredient, which may be dimethicone and caprylyl methicone, among others.

Non-limiting example of preserving agent which can be used in accordance with the invention include phenoxyethanol.

Suitable solvents include, but are not limited to water, 012-15 alkyl benzoate, pentylene glycol, caprylyl glycol, and mixtures thereof.

Adequate surfactants may be selected from potassium cetyl phosphate, sodium methyl stearoyl taurate and inulin lauryl carbamate, among others.

In various embodiments, the solvent is present in a concentration from about 15 to 100% by weight, or from about 25 to about 80% by weight, or from about 30 to about 70% by weight, or from about 35 to about 75% by weight, or preferably from about 40 to about 70% by weight, and more preferably from about 40 to about 60% by weight, including ranges and sub-ranges therebetween, based on the total weight of the combinations and/or compositions of the present disclosure.

Suitable additional actives include, but are not limited to, disodium EDTA, triethanolamine, and mixtures thereof.

The composition may comprise at least one dye/pigment, preferably titanium oxide or iron oxides.

Exemplary fat or oil materials include, but are not limited to, isopropyl lauroyl sarcosinate, stearyl alcohol, and mixtures thereof.

The composition may also comprise at least one filler, such as silica or polylactic acid.

The additional ingredients may represent from 50% to 85%, such as from 55% to 82% or such as from 60 to 80% by weight of the total weight of the composition.

By way of non-limiting illustration, the invention will now be described with reference to the following examples.

EXAMPLES

Examples 1 to 8

A suitable composition according to the state of the art is as Examples 1 and 2, and a suitable composition according to the present invention is as Examples 3 to 8, as follows:

| FUNCTION | INGREDIENT | Ex. 1 (%) | Ex. 2 (%) | Ex. 3 (%) | Ex. 4 (%) | Ex. 5 (%) | Ex. 6 (%) | Ex. 7 (%) | Ex. 8 (%) |
|---|---|---|---|---|---|---|---|---|---|
| ACTIVE COMPOUND | CAPRYLOYL SALICYLIC ACID | 0.15 | 0.15 | 0.1 | 0.05 | 0.5 | 2.5 | 1.25 | 0.016 |
| ACTIVE COMPOUND | NEOHESPERIDIN DIHYDRO-CHALCONE | 0.2 | 0.2 | 0.2 | 1.5 | 1 | 0.05 | 0.25 | 0.016 |
| ACTIVE COMPOUND | DIPOTASSIUM GLYCYRRHIZATE | 0.1 | 0.1 | 0.2 | 3 | 2 | 0.5 | 0.05 | 0.02 |
| VITAMIN | TOCOPHERYL ACETATE | — | 0.5 | — | — | — | — | — | — |
| VITAMIN | TOCOPHEROL | — | — | 0.1 | 1.8 | 2 | 0.5 | 1 | 0.05 |
| SUN FILTER | BUTYL METHOXYDIBENZOYL-METHANE | — | — | 3 | 2.5 | 3 | 3.5 | 4 | 4.5 |
| SUN FILTER | ETHYLHEXYL SALICYLATE | — | — | 5 | 4.5 | 4 | 3.5 | 3 | 5.5 |
| SUN FILTER | TITANIUM DIOXIDE | — | — | 1 | 1 | 1 | 1 | 1 | 1 |
| SUN FILTER | ETHYLHEXYL TRIAZONE | — | — | 3.5 | 3 | 2.4 | 4 | 3.5 | 1.5 |
| SUN FILTER | TEREPHTHALYLIDENE DICAMPHOR SULFONIC ACID | — | — | 3 | 3 | 3 | 3 | 3 | 3 |
| SUN FILTER | OCTOCRYLENE | — | — | 2.5 | 4 | 2.5 | 2.5 | 2.5 | 2.5 |
| SUN FILTER | HOMOSALATE | — | — | 6 | 3 | 4 | 5 | 6 | 6 |
| SUN FILTER | DROMETRIZOLE TRISILOXANE | — | — | 3 | 1.5 | 3 | 3 | 3 | 3 |
| SUN FILTER | BIS-ETHYLHEXYLOXYPHENOL METHOXYPHENYL TRIAZINE | — | — | 3 | 4 | 3.5 | 3 | 2.5 | 6 |
| ACTIVE COMPOUND | DISODIUM EDTA | 0.1 | 0.1 | 0.1 | 0.2 | 0.5 | 0.1 | 0.1 | 0.1 |
| ACTIVE COMPOUND | SODIUM HYALURONATE | 0.4 | 0.2 | — | — | — | — | — | — |
| ACTIVE COMPOUND | ADENOSINE | 0.1 | 0.1 | — | — | — | — | — | — |
| ACTIVE COMPOUND | HYDROXYETHYLPIPERAZINE ETHANE SULFONIC ACID | 5 | 2 | — | — | — | — | — | — |
| ACTIVE COMPOUND | CITRIC ACID | 0.04 | — | — | — | — | — | — | — |
| ACTIVE COMPOUND | TRIETHANOLAMINE | — | — | 0.82 | 0.82 | 1.12 | 1.02 | 1.12 | 1.12 |
| DYE/PIGMENT | RED 4 | 0.00009 | 0.00003 | — | — | — | — | — | — |
| DYE/PIGMENT | IRON OXIDES | — | — | 3.1 | 1.63 | 1.63 | 2.55 | 3.1 | 1.1 |
| DYE/PIGMENT | TITANIUM DIOXIDE | — | — | 6.85 | 8.32 | 7 | 7.4 | 6.5 | 8.32 |
| FATTY COMPOUND | OCTYLDODECANOL | 0.5 | — | — | — | — | — | — | — |
| FATTY COMPOUND | CETEARYL ETHYLHEXANOATE (AND) ISOPROPYL MYRISTATE | — | 0.75 | — | — | — | — | — | — |
| FATTY COMPOUND | ISOPROPYL PALMITATE | — | 1.5 | — | — | — | — | — | — |
| FATTY COMPOUND | *PRUNUS ARMENIACA* (APRICOT) KERNEL OIL | — | 1 | — | — | — | — | — | — |
| FATTY COMPOUND | HYDROGENATED LECITHIN | — | 0.75 | — | — | — | — | — | — |
| FATTY COMPOUND | ISOPROPYL LAUROYL SARCOSINATE | — | — | 1 | 2 | 1 | 3 | 1 | 1 |
| FATTY COMPOUND | STEARYL ALCOHOL | — | — | 1 | 1 | 2 | 1 | 3 | 1 |
| FILLER | SILICA | — | 0.5 | 5 | 5 | 5 | 5 | 5 | 5 |
| FRAGRANCE | FRAGRANCE | 0.15 | 0.25 | 1 | 1 | 1 | 1 | 1 | 1 |
| POLYMER | XANTHAN GUM | 0.1 | — | 0.15 | 0.30 | 0.45 | 0.15 | 0.5 | 0.15 |
| POLYMER | CARBOMER | — | 0.2 | — | — | — | — | — | — |
| POLYMER | ACRYLATES/$C_{10-30}$ ALKYL ACRYLATE CROSSPOLYMER | — | 0.3 | 0.3 | 0.3 | 0.3 | 0.3 | 0.3 | 0.3 |
| POLYMER | AMMONIUM POLYACRYLOYL-DIMETHYL TAURATE | 0.3 | 0.25 | — | — | — | — | — | — |
| POLYMER | PEG/PPG/POLYBUTYLENE GLYCOL-8/5/3 GLYCERIN | — | 0.5 | — | — | — | — | — | — |
| POLYMER | POLY $C_{10-30}$ ALKYL ACRYLATE | — | — | 0.8 | 1 | 1.2 | 3 | 2.3 | 0.8 |
| POLYMER | ALUMINUM STARCH OCTENYLSUCCINATE | — | — | 3 | 3 | 3 | 3 | 3 | 3 |

-continued

| FUNCTION | INGREDIENT | Ex. 1 (%) | Ex. 2 (%) | Ex. 3 (%) | Ex. 4 (%) | Ex. 5 (%) | Ex. 6 (%) | Ex. 7 (%) | Ex. 8 (%) |
|---|---|---|---|---|---|---|---|---|---|
| POLYMER | STYRENE/ACRYLATES COPOLYMER | — | — | 2 | 2 | 2 | 2 | 2 | 2 |
| PRESERVATIVE | PHENOXYETHANOL | 0.3 | 0.25 | 0.7 | 07 | 0.7 | 0.7 | 0.7 | 0.7 |
| SILICON | DIMETHICONE | 1 | 2 | 0.5 | 0.5 | 0.5 | 0.5 | 0.5 | 0.5 |
| SILICON | DIMETHICONE (AND) DIMETHICONE CROSSPOLYMER | — | 1 | — | — | — | — | — | — |
| SILICON | CAPRYLYL METHICONE | 1 | 1 | 1 | 1 | 1 | 1 | | |
| SURFACTANT | PEG-20 METHYL GLUCOSE SESQUISTEARATE | 0.1 | — | — | — | — | — | — | — |
| SURFACTANT | POTASSIUM CETYL PHOSPHATE | — | — | 1 | 1 | 1 | 1 | 1 | 1 |
| SURFACTANT | SODIUM METHYL STEAROYL TAURATE | — | — | | | 0.5 | 0.5 | 0.5 | 0.5 |
| SURFACTANT | INULIN LAURYL CARBAMATE | — | — | 1.3 | 2 | 0.75 | 1.6 | 2.3 | 1.0 |
| VEGETAL EXTRACT | *ZINGIBER OFFICINALE* (GINGER) ROOT EXTRACT (AND) *SANGUISORBA OFFICINALIS* ROOT EXTRACT (AND) *CINNAMOMUM CASSIA* BARK EXTRACT | — | — | 0.15 | 1 | 2.5 | 0.15 | 4 | 3.15 |
| SOLVENT | BUTYLENE GLYCOL | 4.8 | 7 | — | — | — | — | — | — |
| SOLVENT | ALCOHOL DENAT | 5 | 5 | — | — | — | — | — | — |
| SOLVENT | GLYCERIN | 3 | 8 | — | — | — | — | — | — |
| SOLVENT | CAPRYLYL GLYCOL | 0.3 | 0.25 | 0.5 | 0.5 | 0.5 | 0.5 | 0.5 | 0.5 |
| SOLVENT | $C_{12-15}$ ALKYL BENZOATE | — | — | 3 | 2 | 2.6 | 2.5 | 3 | 3 |
| SOLVENT | PENTYLENE GLYCOL | — | — | 2 | 3 | 4 | 1.75 | 2 | 2 |
| SOLVENT | WATER | Q.S. | Q.S. | Q.S. | Q.S. | Q.S. | Q.S. | Q.S. | Q.S. |

Example 9

A non-limiting example regarding the preparation of the composition of Examples 3 to 8, could be as follows:

Step (A): the oil phase comprising the oil raw materials is mixed, and heated up to 75° C.;

Step (B): the aqueous phase comprising the aqueous raw materials is mixed until complete homogenization, and heated up to 75° C.;

Step (C): the aqueous phase of step (B) is added to the oil phase of step (A), after which the emulsifier is subsequently added, followed by mixing the mixture;

Step (D): the polymers are added to the mixture obtained in step (C), subsequently followed by a neutralization;

Step (E): the fillers are gradually added to the mixture obtained in step (D) and mixed until homogeneity, at a temperature of below 30° C.

Example 10

An in vitro study was conducted in order to evaluate the efficacy of the UVA protection (PF-UVA) and critical wavelength of the composition of Example 3, in which the tested samples were evenly applied into four PMMA plates, followed by exposure to UV radiation according to the ISO 24443 "Determination of sunscreen UVA photoprotection in vitro" (2012).

| | PF-UVA and wavelength testing | | |
|---|---|---|---|
| Composition | Average PF-UVA | CI[%] (%)* | Average critical wavelength (nm) |
| Example 1 | 20.5 | 1.9 | 383 |

*Confidence Interval.

The composition of Example 3 has an average PF-UVA of 20.5, and an average critical wavelength of 383 nm.

Example 11

An in-vivo study was conducted with 60 volunteers, women, having solar hyperchromia, during 56 days, in order to evaluate the progressive whitening efficacy of the composition of Example 4. The clinical evaluation of hyperpigmentation was measured using a Dermascore® after 28 and 56 days in normal use conditions under dermatological control.

Through clinical study of the hyperpigmentation degree of right and/or left cheek skin with Dermascore®, as applicable, it was observed a significant decrease in the hyperpigmentation degree from 7.1% in D28 (FIG. 2 (*b*)) and 10.5% in D56 (FIG. 2 (*c*)), when compared to D0 (FIG. 2 (*a*)) (values of $p<0.001$).

The invention was capable to promote a reduction on hyperpigmentation degree on the subject's skin after 28 and 56 days using the product.

Example 12

An in-vivo study was conducted with 50 adult volunteers, men and women between 18 and 66 years old, for four weeks, in order to evaluate the cutaneous acceptability of the composition of Example 5 used in normal conditions under dermatological control.

The product was used during 28 days by the 50 adults, phototypes III and IV, white and black. All subjects were considered as sensitive face skin.

After 28 days of product use, subjects were requested to return to the research institute, where the dermatologist performed a final cutaneous examination.

As a conclusion, the composition according to Example 5 is cutaneous safe.

The invention claimed is:

1. A sun care composition for whitening a skin, comprising:
   (a) a UVA filter system;
   (b) a whitening system configured to act at different levels of pigmentation of melasma for whitening the skin, the whitening system including at least neohesperidin dihydrochalcone, capryloyl salicylic acid, and dipotassium glycyrrhizate; and
   (c) a combination of at least two antioxidants selected from at least one vitamin and at least one vegetal extract,
   wherein the at least one vitamin is selected from tocopherol, and the at least one vegetal extract is selected from *Zingiber officinale* (ginger) root extract, *Sanguisorba officinalis* root extract, *Cinnamomum cassia* bark extract or their mixtures.

2. The composition according to claim 1, wherein the UVA filter system includes UV filters selected from butyl methoxydibenzoylmethane, bis-ethylhexyloxyphenol methoxyphenyl triazine, and ethylhexyl triazone.

3. The composition according to claim 1, wherein an amount of the UVA filter system is from about 1% to about 15% by weight, based on the total weight of the composition.

4. The composition according to claim 1, wherein an amount of the UVA filter system is from about 5% to about 10% by weight, based on the total weight of the composition.

5. The composition according to claim 1, wherein the UVA filter system employs a first UVA filter in an amount ranging from about 1% to about 7% by weight, including all ranges and sub-ranges there between, relative to the total weight of the composition.

6. The composition according to claim 1, wherein the UVA filter system employs a first UVA filter in an amount ranging from about 2.5% to about 4% by weight, including all ranges and sub-ranges there between, relative to the total weight of the composition.

7. The composition according to claim 1, wherein the whitening system employs a second UVA filter in an amount ranging from about 1% to about 7% by weight, including all ranges and sub-ranges there between, relative to the total weight of the composition.

8. The composition according to claim 1, wherein the whitening system employs a second UVA filter in an amount ranging from about 2.5% to about 4% by weight, including all ranges and sub-ranges there between, relative to the total weight of the composition.

9. The composition according to claim 1, wherein the whitening system employs a third UVA filter in an amount ranging from about 1% to about 7% by weight, including all ranges and sub-ranges there between, relative to the total weight of the composition.

10. The composition according to claim 1, wherein the whitening system employs a third UVA filter in an amount ranging from about 2% to about 5% by weight, including all ranges and sub-ranges there between, relative to the total weight of the composition.

11. The composition according to claim 1, wherein an amount of the whitening system is from about 0.05% to about 5% by weight, including all ranges and sub-ranges there between, relative to the total weight of the composition.

12. The composition according to claim 1, wherein an amount of the whitening system is from about 0.1% to about 2.5% by weight, including all ranges and sub-ranges there between, relative to the total weight of the composition.

13. The composition according to claim 1, wherein the whitening system employs neohesperidin dihydrochalcone in an amount ranging from about 0.05% to about 3% by weight, including all ranges and sub-ranges there between, relative to the total weight of the composition.

14. The composition according to claim 1, wherein the whitening system employs neohesperidin dihydrochalcone in an amount ranging from about 0.1% to about 1.5% by weight, including all ranges and sub-ranges there between, relative to the total weight of the composition.

15. The composition according to claim 1, wherein the whitening system employs capryloyl salicylic acid in an amount ranging from about 0.05% to about 2.5% by weight, including all ranges and sub-ranges there between, relative to the total weight of the composition.

16. The composition according to claim 1, wherein the whitening system employs capryloyl salicylic acid in an amount ranging from about 0.05% to about 1.5% by weight, including all ranges and sub-ranges there between, relative to the total weight of the composition.

17. The composition according to claim 1, wherein the whitening system employs dipotassium glycyrrhizate in an amount ranging from about 0.05% to about 3% by weight, including all ranges and sub-ranges there between, relative to the total weight of the composition.

18. The composition according to claim 1, wherein the whitening system employs dipotassium glycyrrhizate in an amount ranging from about 0.1% to about 2% by weight, including all ranges and sub-ranges there between, relative to the total weight of the composition.

19. The composition according to claim 1, wherein the combination of at least one antioxidant vitamin and at least one antioxidant vegetal extract is selected from tocopherol and a vegetal extract comprising *Zingiber officinale* (ginger) root extract, *Sanguisorba officinalis* root extract and *Cinnamomum cassia* bark extract.

20. The composition according to claim 1, wherein an amount of the combination of at least two antioxidants is from about 0.05% to about 5% by weight, including all ranges and sub-ranges there between, relative to the total weight of the composition.

21. The composition according to claim 1, wherein an amount of the combination of at least two antioxidants is from about 0.1% to about 2.5% by weight, including all ranges and sub-ranges there between, relative to the total weight of the composition.

22. The composition according to claim 1, wherein the combination of at least two antioxidants employs a vitamin in an amount ranging from about to about 2.5% by weight, including all ranges and sub-ranges there between, relative to the total weight of the composition.

23. The composition according to claim 1, wherein the combination of at least two antioxidants employs a vitamin in an amount ranging from about to about 1.5% by weight, including all ranges and sub-ranges there between, relative to the total weight of the composition.

24. The composition according to claim 1, wherein the combination of at least two antioxidants employs a vegetal extract in an amount ranging from about 0.05% to about 3.75% by weight, including all ranges and sub-ranges therebetween, relative to the total weight of the composition.

25. The composition according to claim 1, wherein the combination of at least two antioxidants employs a vegetal extract in an amount ranging from about 0.1% to about 2% by weight, including all ranges and sub-ranges therebetween, relative to the total weight of the composition.

26. The composition according to claim 1, wherein the composition has a pH within the range of about 5.5 to about 7.0.

27. The composition according to claim 1, wherein the composition has a pH of about 6.5.

28. The composition according to claim 1, further comprising at least one additional UV filter.

29. The composition according to claim 1, further comprising cosmetically acceptable ingredients selected from perfume/fragrance, polymers, preserving agents, solvents, additional actives, surfactants, fat materials, vitamins, fillers and mixtures thereof.

30. The composition according to claim 1, further comprising a Sun Protection Factor ranging from 30 to 80.

31. The composition according to claim 1, further comprising a Sun Protection Factor is about 60.

32. A method of using the sun care composition, of claim 1, comprising applying the composition to the skin, wherein the composition is to be used for whitening the skin.

33. The method according to claim 32, wherein the composition is for progressive whitening of the skin, while preventing further damages from UVA radiation.

34. A process of manufacture of the sun care composition, as defined in claim 1, comprising:
 (A): an oil phase comprising the oil raw materials to be mixed, and heated up to
 (B): an aqueous phase comprising the aqueous raw materials to be mixed until complete homogenization, and heated up to 75° C.;
 (C): the aqueous phase of step (B) is added to the oil phase of step (A), after which an emulsifier is subsequently added, followed by mixing the mixture;
 (D): the polymers are added to the mixture obtained in step (C), subsequently followed by a neutralization; and
 (E): the fillers are gradually added to the mixture obtained in step (D) and mixed until homogeneity, at a temperature of below 30° C.

* * * * *